United States Patent [19]

Pinschmidt, Jr. et al.

[11] Patent Number: 4,906,777
[45] Date of Patent: Mar. 6, 1990

[54] SYNTHESIS OF ETHYLIDENE BIS-FORMAMIDE USING FORMIC ACID

[75] Inventors: Robert K. Pinschmidt, Jr., Allentown; Andrew F. Nordquist, Whitehall, both of Pa.

[73] Assignee: Air Products and Chemicals, Inc., Allentown, Pa.

[21] Appl. No.: 260,090

[22] Filed: Oct. 19, 1988

[51] Int. Cl.$^4$ .............................................. C07C 67/20
[52] U.S. Cl. ..................................................... 564/215
[58] Field of Search ......................................... 564/215

[56] References Cited

U.S. PATENT DOCUMENTS

| | | | |
|---|---|---|---|
| Re. 30,362 | 8/1980 | Gless, Jr. et al. | 564/215 |
| 4,018,826 | 4/1977 | Gless, Jr. et al. | 260/583 |
| 4,322,271 | 3/1982 | Jensen et al. | 204/73 R |
| 4,490,557 | 12/1984 | Dawson et al. | 564/159 |
| 4,567,300 | 1/1986 | Murao et al. | 564/215 |
| 4,578,515 | 3/1986 | Dawson et al. | 564/215 |
| 4,670,591 | 6/1987 | Oftring et al. | 564/224 |

FOREIGN PATENT DOCUMENTS 3443463  5/1986  Fed. Rep. of Germany .

OTHER PUBLICATIONS

Dawson et al., "Poly(vinylamine hydrochloride), Synthesis and Utilization for the Preparation of Water-Soluble Polymeric Dyes"; JACS, 98, pp. 5996–6000 (1976).

Krimmel et al., "The Synthesis of Fluorine-Containing Aliphatic gem-Dinitramines", Journal of Organic Chemistry, vol. 36, No. 2, p. 351 (1971).

Summerville et al., "Synthesis of N-Vinyl Acetamide and Preparation of Same, Polymers and Copolymers", ACS Polymer Reprints (1983), 24(2), pp. 12–13.

*Primary Examiner*—Anton H. Sutto
*Attorney, Agent, or Firm*—Mark L. Rodgers; William F. Marsh; James C. Simmons

[57] ABSTRACT

Ethylidene bis-formamide, a precursor for the monomer N-vinylformamide, is made in high yield by heating together formamide and acetaldehyde in a mol ratio of at least 3:1 and in a reaction mixture which is at least 20 weight percent formic acid. In a preferred procedure the acetaldehyde is added after the formamide has been preheated and formic acid is present. Yields of ethylidene bis-formamide of over 50%, based on the acetaldehyde, are obtained in relatively short reaction times, before loss of substantial amounts of recoverable formamide through hydrolysis.

9 Claims, No Drawings

SYNTHESIS OF ETHYLIDENE BIS-FORMAMIDE USING FORMIC ACID

TECHNICAL FIELD OF INVENTION

The present invention relates to a process for making ethylidene bis-formamide from acetaldehyde and formamide.

BACKGROUND OF THE INVENTION

Poly(vinylamines) are polymers which can be prepared over a broad range of molecular weights. Depending upon their average molecular weight, such polymers find various uses in the preparation of dyes, pharmaceuticals, flocculation agents and as viscosifiers in papermaking and enhanced recovery of oil. Because vinylamines are too unstable to be polymerized, these polymers are prepared by hydrolysis of poly(N-vinylamides) such as poly(N-vinylacetamide). The monomer for this polymer is made by the reaction of acetamide and acetaldehyde to form ethylidene bis-acetamide which is then pyrolyzed to the N-vinylacetamide. This reaction is described in Dawson, et. al. JACS, 98, pg. 5996–6000 (1976). An improvement in the basic process is described as a reaction between acetamide and acetaldehyde over a sulfuric acid catalyst, rather than perchloric acid, in order to form ethylidene bis-acetamide which was then pyrolyzed to form N-vinylacetamide. The N-vinylacetamide was polymerized and the polymer subjected to hydrolysis to form poly(vinylamine hydrochloride) which was used in preparing polymeric azo dyes.

U.S. Pat. No. 4,018,826 (1977) also discloses a method of making poly(vinylamine) by hydrolyzing poly(N-vinylacetamide) which has been formed by thermally cracking ethylidene bis-acetamide prepared by reacting acetaldehyde and acetamide using an aqueous mineral acid catalyst.

It was known that a similar reaction could take place between formamide and acetaldehyde in an aqueous solution of hydrochloric acid as described in "Journal of Organic Chemistry", Volume 36, No. 2, pg. 351 (1971), which describes a method for making 1,1-bis(-formamido)ethane, another name for ethylidene bis-formamide.

U.S. Pat. No. 4,490,557 (1984) discloses the preparation of ethylidene bis-formamide from acetaldehyde and formamide using an acidic catalyst and an ammonia scavenger, such as acetic anhydride. Wiped film evaporation is used to recover the ethylidene bis-formamide which can be cracked to form N-vinylformamide, a monomer useful in preparing poly(N-vinylformamide) which can then be hydrolyzed to poly(vinylamines), useful in making dyes and pharmaceuticals. The acidic catalysts which are disclosed include acidic ion exchange resins, of which several examples are given including the preferred operating example. Alternatively, mineral acids, such as sulfuric or hydrochloric acid, or lower alkanoic acids, such as formic or acetic acids, can be used when added in catalytically effective amounts. Although such amounts are stated to cover a broad range from about 0.001 to 1 mole of acid catalyst per mole of formamide, the preferred catalytically effective amount is 0.002 to 0.1 mole of catalyst per mole of formamide and there is no suggestion of any advantage in using solvent quantities of any of the acids in the reaction mixture.

Because of the difficulty in recovering polymerization grade monomers by the above described routes, others have sought to prepare N-vinylcarboxylic acid amides by different routes. U.S. Pat. No. 4,322,271 (1982) discloses that N-vinyl-N-alkyl-carboxylic acid amides can be obtained by removing an alcohol from N-α-alkoxyethyl-N-alkyl-carboxylic acid amides which have been made by prior alkylation and alkoxylation steps from N-ethyl-carboxylic acid amides.

Sommerville, et. al., ACS, *Polymer Preprints*, (1983) 24, 12–13, discloses preparing N-vinylacetamide from acetamide and the acetaldehyde dimethyl acetal. This process requires large excesses of the acetal, for example mole ratios of about 20 moles of acetal per mole of acetamide, in order to achieve practical yields and purities and is reported to fail in the corresponding reaction with formamide.

U.S. Pat. No. 4,567,300 (1986) discloses, on the other hand, reacting formamide with acetaldehyde over a basic catalyst to form N-(α-hydroxyethyl)-formamide instead of ethylidene bis-formamide. This process is unattractive because it requires two discrete steps, plus the handling of a solid intermediate and the disposal of salts.

U.S. Pat. No. 4,670,591 (1987) describes the synthesis of N-alkoxyethyl formamide from vinylether and formamide. While this process is said to be effective with either an acidic or basic catalyst, the vinylethers are very expensive starting materials.

German Patent DE3443463 (1986) describes making N-vinylformamide using 1-cyanoethyl formamide. This process has the disadvantage of generating hydrogen cyanide which is very toxic.

The above processes as routes to the manufacture of poly(vinylamines) all have the disadvantage of difficult catalyst removal, toxic byproduct formation, low conversions or catalyst deactivation. A commercially practicable process which does not have these disadvantages has yet to be developed. Ethylidene bis-formamide is still an attractive intermediate for the synthesis of N-vinylformamide as this product is stable and can be efficiently cracked thermally to form a 1:1 mixture of N-vinylformamide and formamide. Such a mixture can be purified by distillation as described in U.S. Pat. No. 4,578,515.

The preparation of ethylidene bis-formamide using strong acid ion exchange resins as disclosed in U.S. Pat. No. 4,490,557, has the disadvantage that the strong acid catalyst residues must be removed from the ethylidene bis-formamide product prior to purification and cracking. Otherwise unwanted side reactions and loss of N-vinylformamide due to acid catalyzed degradation in the cracking step are observed. The use of the solid polymer acid resins, on the other hand, allows the removal of salts and catalyst as a solid from the liquid product. Unfortunately, however, in the synthesis of ethylidene bis-formamide the catalyst activity declines rapidly during the reaction, giving poor conversions. This is caused by the hydrolysis of formamide and neutralization of the catalyst with ammonia. Since water is produced in the synthesis of ethylidene bis-formamide and high levels of formamide are required to drive the synthesis reaction, it is not feasible to suppress the formation of ammonia using prior art technology. The result is poor conversions and impure product, probably arising from unwanted acetaldehyde self-condensation reactions. It is highly desirable, therefore, to find a way of improving the yields of ethylidene bis-formamide in such reactions and reducing the loss of formamide by hydrolysis.

BRIEF SUMMARY OF THE INVENTION

The present invention provides a method of making ethylidene bis-formamide in excellent yields, above 50% based on the acetaldehyde, and readily achieving 100% yield with reduced loss of formamide which can be recovered and reused in the process. It has been found that the reaction of formamide and acetaldehyde can be controlled to achieve such results in the formation of ethylidene bis-formamide by using very high levels of formic acid, i.e., in solvent quantities which make up at least 20 wt. % of the reaction mixture. Also the mole ratio of the formamide to acetaldehyde should be at least 3:1.

The reaction for making ethylidene bis-formamide according to a preferred aspect of the invention includes the preparation of a reaction mixture of formamide, acetaldehyde and formic acid by first preheating the formamide, either with or without formic acid present, to a temperature between 35° C. and the reaction temperature, mixing the formamide either before, during or following the preheating step with an amount of formic acid which is sufficient to make up at least 20 wt.% of the total reaction mixture, and adding an amount of acetaldehyde to the preheated formamide in the presence of formic acid sufficient to make the mole ratio of the unreacted formamide to acetaldehyde in the range of 3:1 to 10:1. The reaction mixture is then heated, if necessary, to the reaction temperature which is in the range of 50°–120° C., held at the reaction temperature for a time sufficient to convert at least 50 mole % of the acetaldehyde to ethylidene bis-formamide, and then the formic acid and at least part of the unreacted formamide are separated from the ethylidene bis-formamide.

DETAILED DESCRIPTION OF THE INVENTION

Formic acid present in high concentrations as required by this invention provides sufficient acidity to catalyze efficiently the synthesis of ethylidene bis-formamide. In addition, the use of solvent quantities of formic acid increases the conversion and decreases by-product formation. The formamide hydrolysis which inactivates stronger acid catalysts presents no problem in the invention because formic acid is regenerated as shown by the following equation:

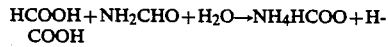

$$HCOOH + NH_2CHO + H_2O \rightarrow NH_4HCOO + HCOOH$$

Although an equivalent of salt is produced in this reaction, the concentration of formic acid remains the same. Also ammonium formate can be dehydrated back to formamide on heating above about 170° C. This not only enables the regeneration of formamide lost to the hydrolysis side reaction, but eliminates the problem of having to dispose of non-volatile salts present, such as when mineral acids are used. Also formic acid can be conveniently removed by distillation, thus avoiding a solids handling problem and a costly catalyst regeneration step as when acidic resin catalysts are employed.

The formic acid is present in the reaction mixture with acetaldehyde and formamide in solvent quantities, making up at least 20 wt.% of the reaction mixture. It is preferred that sufficient formic acid be used to make up from ¼ to ⅝ by weight of the reaction mixture. In general, the reaction temperature should be in the range of 50° C. to 120° C. and better results are obtained in terms of overall yield and conversion when the temperature is in the range of 60° C. to 100° C. It has been found that 100% conversion of acetaldehyde to ethylidene bis-formamide can be obtained using sufficient formic acid to make up at least about 45 wt.% of the reaction mixture, when the mole ratio of formamide to acetaldehyde is also in a preferred range of about 4:1 to 6:1 and the reaction temperature is in a preferred range of about 60° C. to 85° C.

Reaction pressures can vary from sub-atmospheric to super-atmospheric pressure, but it is preferred to operate at either atmospheric pressure or at a sub-atmospheric pressure in order to remove a water/formic acid azeotrope during the reaction. The presence of water should be minimized and although the reaction can be run with miscible or immiscible inert solvents, it is preferred to use the reactants alone since the formic acid is sufficient to provide the reaction mass necessary for adequate mixing and temperature control. In this way the formic acid serves not only to catalyze the reaction but also to assist in the control of process conditions and supression of unwanted side reactions.

The ratio of formamide to acetaldehyde should be at least 3:1 and can run as high as 10:1, on a mole basis. The preferred ratios are 4:1 to 6:1. The formamide is preheated to a temperature between 35° C. and the reaction temperature and the formic acid can be added either concurrently with the acetaldehyde or before any of the acetaldehyde is added to the reaction mixture. Addition of the acetaldehyde slowly aids in maintaining the high formamide to acetaldehyde ratio which is desired.

The reaction mixture is held at the reaction temperature for a sufficient time to convert at least 50 mole % of the acetaldehyde to ethylidene bis-formamide and preferably the conversion is sufficient to produce from 70–100% yield of ethylidene bis-formamide based on the acetaldehyde. Although some of the formic acid can be added to the formamide concurrently with the acetaldehyde, it is preferred that the formic acid be added so that at least 50 wt.% of the acetaldehyde is added after the formamide and the formic acid have been mixed in the proportions required for the reaction mixture.

The reaction can be conducted either continuously or by batch or semi-batch operation and the reaction time during which the reagents are heated at the desired temperature can be from 0.1 to 24 hours, but is preferably from 0.25 to 8 hours. It is desirable to operate under conditions so that the reaction can be terminated in about 0.5 to 2 hours in order to minimize hydrolysis of the formamide. The water which is formed in the reaction can be distilled out as it is formed as a formic acid azeotrope or in the form of a binary or terinary azeotrope with other co-solvents such as toluene, hexane and the like.

When the reaction is complete, having achieved the desired yield of ethylidene bis-formamide, the product can be concentrated by short contact time flash distillation, as for example by using a wiped filmed evaporator as described in U.S. Pat. No. 4,578,515 (1986). Alternatively, the ethylidene bis-formamide can be isolated by crystallization or solvent extraction. The formic acid can be readily removed from the reaction products by distillation and both the formic acid and at least part of the unreacted formamide separated in this manner can be reused in the reaction by recycling to the reaction mixture after suitable purification steps have been carried out. The crude product mixture contains ammonium formate salt as a byproduct, but these salts do not interfere with ethylidene bis-formamide pyrolysis over quartz chips in the formation of N-vinylformamide. Also ammonium formate can be efficiently dehydrated to formamide during the pyrolysis reaction. The presence of either ammonium formate or any residual formic acid does not appear to interfere seriously with the stability of the dry N-vinyl formamide. While not to be bound by theory, it is possible that the high formic acid concentration which is used in this invention in combination with the other conditions of the process produces a high polarity medium which aids in the synthesis of ethylidene bis-formamide.

EXAMPLE 1

A stirred flask, having a water cooled condenser and an oil sealed nitrogen atmosphere, was charged with 256.3 g (5.67 moles) of formamide and 253.1 g (5.39 moles) of 98% formic acid. The flask was heated to 45° C. in an oil bath and 39.1 g (0.889 moles) of acetaldehyde was added via an addition funnel at a rate which minimized acetaldehyde loss from the system. The temperature was increased to 80° C. over a period of 20 minutes and held at 80° C. for an additional 100 minutes, producing a reaction mix containing 24.0% formamide and 18.8% ethylidene bis-formamide (BIS) by gas chromatographic analysis, plus water, ammonium formate and formic acid.

The reaction mix was concentrated by stripping formic acid and formamide at 115° C. and 7 Torr for 45 minutes using a short path (Kugelrohr) still. The 202.4 g of concentrated product contained 38.9% ethylidene bis-formamide, 31.6% formamide, 1.7% ammonium formate, and 3.2% water.

This Example shows the production of ethylidene bis-formamide after only 2 hours in a high yield of 76.3% based on the starting molar amount of acetaldehyde. Formic acid made up 45.2 wt.% of the reaction mixture and the mole ratio of formamide to acetaldehyde was 6.4.

EXAMPLES 2-5

A concentrate at pH 3.96, prepared by Kugelrohr distillation as in Example 1, and containing 42.6% BIS, 37% formamide, 3.2% water, and 1.96% ammonium formate was vacuum pyrolyzed as follows, and the results are given in Table 1. The concentrate, heated to 105° C. to dissolve crystalline BIS, was passed from an atmospheric pressure reservoir through a flow regulating orifice into the evacuated zone, where it was diluted with 20 sccm of nitrogen before passing to the preheater. The preheater, a vertical, downflow 18.3 cm long×1.18 cm I.D. 316 stainless steel tube, packed with ⅛ in. stainless steel helices, was heated such that the vapor exiting this bed was at 250° C. Mid-bed temperature of the preheater was 174°-227° C. Preheated vapor passed through 5 cm of open tube to the reactor zone composed of 26.7 g of 10/16 mesh quartz chips packed in a vertical 28.5 cm long×1.18 cm I.D. heated tube. The condensible component of the effluent was trapped at 0° C. and 18-20 Torr. Gaseous products were purged.

Prior to obtaining the results in Table 1, the bed was equilibrated by passing 60.6 g feed through the reactor at 400° C.

TABLE 1

| Example | Feed Rate (g/h) | Reactor Hot Spot (°C.) | BIS Pyrolysis Product Composition (Wt %) NVF | BIS | BIS Conv (%) | Molar Selectivity (%) | Product pH |
|---|---|---|---|---|---|---|---|
| 2 | 45.3 g | 415 | 22.1 | 7.5 | 83.0 | 99.0 | 7.45 |
| 3 | 46.7 g | 361 | 19.2 | 10.4 | 75.6 | 97.9 | 6.8 |
| 4 | 43.5 g | 317 | 21.0 | 9.7 | 78.9 | 95.5 | 7.3 |
| 5 | 36.3 g | 468 | 27.9 | 0.8 | 98.6 | 84.0 | 8.3 |

Examples 2-5 demonstrate that the ethylidene bis-formamide formed by the process of this invention can be effectively pyrolyzed to yield the desired N-vinyl formamide (NVF) with good conversions of the ethylidene bis-formamide and a high molar selectivity.

EXAMPLES 6-10

Examples 6 through 10 illustrate some of the reaction recipes applicable to this invention.

The apparatus described in Example 1 was charged with formamide and 98% formic acid as shown in Table 2. After heating the mixture to 45° C., acetaldehyde was added as indicated, while increasing the temperature to 60° C. over a 10 minute period. After periods of 1 hour and 24 hours the reaction was sampled, and the compositions indicated were measured by gas chromatography.

TABLE 2

| Example | Reactant Wt (g) (F) Formamide | (A) Acetaldehyde | Formic Acid (98%) | BIS Synthesis Reactant Wt % Formic Acid | F/A Mol Ratio | Time | Composition (Wt %) Formamide | BIS | F/BIS Ratio | Yield BIS (%) |
|---|---|---|---|---|---|---|---|---|---|---|
| 6 | 100 | 17.2 g | 100 | 45.1 | 5.7 | 1 h | 27.0 | 18.0 | 1.5 | 86.0 |
|   |     |        |     |      |     | 24 h | 21.8 | 20.9 | 1.0 | 100.0 |
| 7 | 100 | 17.3 | 40.6 | 25.2 | 5.7 | 1 h | 49.2 | 9.3 | 5.3 | 32.1 |
|   |     |      |      |      |     | 24 h | 30.1 | 25.0 | 1.2 | 86.4 |
| 8 | 101 | 17.0 | 10.0 | 7.6 | 5.7 | 1 h | 73.0 | 2.45 | 3.0 | 7.0 |
|   |     |      |      |     |     | 24 h | 60.7 | 11.1 | 5.5 | 31.7 |
| 9 | 56 | 16.6 | 37.0 | 33.1 | 3.3 | 1 h | 32.4 | 16.2 | 2.0 | 40.6 |
|   |    |      |      |      |     | 24 h | 20.1 | 25.1 | 0.80 | 63.0 |
| 10 | 36 | 16.2 | 36.2 | 40.2 | 2.2 | 1 h | 19.7 | 18.7 | 1.1 | 38.6 |
|    |    |      |      |      |     | 24 h | 14.7 | 23.6 | 0.62 | 48.9 |

As illustrated by Examples 6–10, when the formic acid was present in the desired proportions making up at least 25 wt.% of the reaction mixture, and the mole ratio of formamide to acetaldehyde was 3 or above, a yield of ethylidene bis-formamide of greater than 50% was achieved after 24 hours. In Example 6, 100% yield was obtained when the formic acid was used in an amount of 45.1 wt.% of the reaction mixture and the ratio of formamide to acetaldehyde was 5.7. On the other hand, with the same formamide to acetaldehyde mole ratio and only 7.6 wt.% of formic acid present in the reaction mixture, as shown by Example 8, the yield of ethylidene bis-formamide was only 7.0% after one hour and 31.7% after 24 hours. Also, Example 10 illustrates that when 40.2 wt.% of formic acid was present and the mole ratio of formamide to acetaldehyde was only slightly above 2:1 stoichiometric combination proportions (2.2), the yield of ethylidene bis-formamide did not exceed 50%, even after 24 hours. Under these conditions it is seen that the amount of formamide in the reaction product after 24 hours is quite low in comparison to the amount of ethylidene bis-formamide, indicating that with low formamide excess, the reaction does not proceed to high conversion.

EXAMPLE 11

The reaction flask of the apparatus described in Example 1 was charged with 100 g formamide and equipped with two addition funnels. After heating to 100° C., addition of 40.5 g formic acid and 13.5 g of acetaldehyde was started simultaneously. Formic acid addition was complete in 5 minutes. Acetaldehyde addition was complete after 18 minutes, when the product contained 16.8% BIS (72.9% yield based on acetaldehyde), and 45.4% formamide. At one hour the product contained 18.8% BIS (81.3% yield).

This examples demonstrates that at 100° C. after only 18 minutes a yield of ethylidene bis-formamide of 72.9% can be achieved. In this reaction the amount of formic acid was 25.9 wt.% of the reaction mixture and the mol ratio of formamide to acetaldehyde was 7.2.

EXAMPLE 12

A flask was charged with 10.00 g (0.227 moles) of formamide, 4.06 g (0.0865 moles) of 98% formic acid, and 1.80 g (0.0409 moles) of acetaldehyde, mixed, and left static at 26° C. After 3 hours the reaction mix contained 4.81% BIS (16.1% yield) and 53.0% formamide. After 5 days the composition was 11.7% BIS (37.5% yield) and 45.4% formamide.

As demonstrated by the this Example, it is impractical to operate the process at a temperature of 26° C. even though the formic acid present made up ¼ of the reaction mixture and the starting mol ratio of formamide to acetaldehyde was 5.6.

EXAMPLE 13

The reaction flask of an apparatus as described in Example 1 was charged with 34.2 g (0.70 moles) of formamide and 2.5 g of Rohm and Haas XN1010 macroreticular sulfonic acid resin. Addition of 5.8 g acetaldehyde over 11 minutes while heating from 60° to 80° C., followed by holding at 80° C. for 140 minutes, yielded a product containing 70.8% formamide, and 21.1% BIS on a catalyst free basis (equivalent to 57% yield). The reaction product was discolored, indicating production of by-product acetaldehyde condensates.

In this Example the use of an acidic ion exchange resin is demonstrated illustrating the disadvantage of byproduct formation when following this synthesis route, even though the yield of ethylidene bis-formamide exceeded 50%.

EXAMPLE 14

The reaction flask of an apparatus as described in Example 1 was charged with 100 g (2.22 moles) of formamide and 1 g of concentrated sulfuric acid. Over 7 minutes 16.2 g of acetaldehyde was added as the reaction was heated to 70° C. One gram of sulfuric acid was added after another 29 minutes and again after another 34 minutes. After 90 minutes the reaction mix contained 25.7% BIS (71% yield) and 66% formamide.

The reaction product was neutralized by slow addition of 2.22 g of calcium hydroxide with stirring, producing a gel. A tediously slow filtration of the gel produced a calcium sulfate-containing filter cake and a BIS/formamide filtrate. The cake was washed with ¼ volume of formamide and the washings combined with the reaction mix filtrate, producing a solution containing 21.9% BIS, and an unquantified amount of calcium sulfate in formamide.

Concentration of the above filtrate by feeding at 7.7 g/min onto a Pope molecular still (wiped film evaporator with 2" diameter×8" long body) evacuated to 20 Torr at a wall temperature of 180°–184° C. and wiper blade speed of 180 RPM resulted in fouling of the wiper flutes with calcium sulfate-containing sludge. The 64.7 g of raffinate contained 42.7% BIS (91% recovery). On crystallization 15.6 g of BIS was isolated.

This Example illustrates that, when using concentrated sulfuric acid as the catalyst for the reaction of formamide and acetaldehyde, even though a fairly high yield of ethylidene bis-formamide was ultimately obtained, the recovery of the desired product involves a time-consuming and costly procedure which cannot compare in commercial potential to the use of the process of the invention where only relatively low boiling formic acid needs to be separated from the reaction product in order to recover reasonably high concentrations of ethylidene bis-formamide.

EXAMPLE 15

The reaction flask of the apparatus in Example 1 was charged with 100 g formamide and 100 g glacial acetic acid. Slow addition of 17.1 g acetaldehyde over 10 minutes while heating to 60° C. and further heating for 120 minutes produced a mix containing 3.8% BIS (19.2% yield) and 38.2% formamide.

This Example shows that acetic acid is not the equivalent of formic acid in the process of this invention.

EXAMPLES 16–22

Examples 16 through 22 illustrate the effect of the presence of water on BIS yield for the process of the present invention.

The apparatus described in Example 1 was charged with formamide and 100% formic acid along with various concentrations of water as shown in Table 3. After heating the mixture to 45° C., acetaldehyde was added as indicated, while increasing the temperature to 80° C. over a ten minute period. The reaction was sampled one hour after acetaldehyde addition, and the compositions indicated were measured by gas chromatography.

TABLE 3

| | | Reactant Wt (g) | | | BIS Synthesis | | | | | | |
|---|---|---|---|---|---|---|---|---|---|---|---|
| Example | (F) Formamide | (A) Acetaldehyde | Formic Acid (100% basis) | Water | Reactant Wt % Formic Acid | $H_2O/A$ Mol Ratio | F/A Mol Ratio | Time | Composition (Wt %) Formamide | BIS | Yield BIS (%) |
| 16 | 135 | 21.6 | 122.5 | 2.5 | 43.5 | 0.28 | 6.11 | 1 hr | 27.5 | 20.2 | 100 |
| 17 | 25 | 2.91 | 24.0 | 1.0 | 44.4 | 0.63 | 6.39 | 1 hr | 30.0 | 17.3 | 90.8 |
| 18 | 25 | 3.85 | 24.0 | 1.51 | 44.2 | 0.96 | 6.35 | 1 hr | 30.6 | 15.3 | 81.9 |
| 19 | 25 | 3.85 | 24.0 | 2.02 | 43.7 | 1.28 | 6.35 | 1 hr | 31.2 | 13.9 | 75.6 |
| 20 | 135 | 21.0 | 121.4 | 16.6 | 41.3 | 1.93 | 6.29 | 1 hr | 33.2 | 11.2 | 59.5 |
| 21* | 250 | 40.7 | 245.0 | 5.0 | 45.3 | 0.30 | 6.00 | 1 hr | 31.1 | 17.4 | 87.9 |
| 22 | 500 | 98.9 | 494.9 | 10.1 | 44.8 | 0.25 | 4.94 | 1 hr | 26.5 | 21.0 | 88.9 |

*Non-standard temperature profile; temperature dropped below 80° C. during reaction.

From the results reported in Table 3, it can be seen that, at fairly constant formic acid concentrations, as the $H_2O$/acetaldehyde ratio increases the BIS yield decreases.

EXAMPLE 23

This Example illustrates the effect of excessively long reaction times. The apparatus described in Example 1 was charged with 135 g formamide and 125 g of 98% formic acid. After heating to 40° C. under nitrogen, 22 g acetaldehyde was added over ten minutes. After an additional five minutes, the temperature was increased to 80° C. and held. The reaction was sampled and the compositions indicated in Table 4 were measured by gas chromatography.

As shown in Table 4, formamide levels in the reaction mix continued to decrease after the ethylidene bisformamide yield was 100% because formamide was hydrolyzed by by-product water. To improve formamide recovery for recycle, formamide hydrolysis can be minimized by separating formic acid from formamide and ethylidene bisformamide when ethylidene bisformamide synthesis is essentially complete. After excessive reaction times (24 hour in this case) formamide not only hydrolyses, but ethylidene bisformamide decomposes slightly.

TABLE 4

| | Composition (wt %) | | | | | |
|---|---|---|---|---|---|---|
| Time | Formic Acid | Formamide | Acetaldehyde | BIS | Water | Ammonium |
| 0 | 44.0 | 47.9 | 7.67 | 0 | 0.45 | 0 |
| 15' | n.a. | 37.3 | 2.68 | 2.6 | n.a. | n.a. |
| 30' | n.a. | 34.0 | 2.61 | 10.1 | 2.4 | 0.6 |
| 1 h | n.a. | 27.5 | 0.31 | 20.2 | 3.1 | 0.6 |
| 2 h | n.a. | 27.2 | 0.15 | 20.2 | 2.9 | 1.3 |
| 4 h | n.a. | 23.2 | 0 | 22.1 | 2.0 | 3.2 |
| 22 h 2348K | n.a. | 19.9 | 0 | 19.9 | 0.65 | 8.4 |

We claim:

1. A process for making ethylidene bis-formamide which comprises heating and contacting formamide and acetaldehyde in a mole ratio of at least 3:1 in formic acid making up at least ¼ by weight of the reaction mixture at a reaction temperature of at least 50° C.

2. A process for making ethylidene bis-formamide which comprises:
   (a) preparing a reaction mixture of formamide, acetaldehyde and formic acid by:
      (i) preheating said formamide, with or without formic acid present, to a temperature between 35° C. and the reaction temperature;
      (ii) mixing with said formamide an amount of formic acid sufficient to make up at least 20 weight percent of said reaction mixture; and
      (iii) adding an amount of acetaldehyde to the preheated formamide in the presence of formic acid sufficient to make the mole ratio of the unreacted formamide to acetaldehyde in the range of 3:1 to 10:1;
   (b) heating said reaction mixture, if necessary, to a reaction temperature in the range of 50° to 120° C.;
   (c) holding said reaction mixture at said reaction temperature for a time sufficient to convert at least 50 mole percent of said acetaldehyde to ethylidene bis-formamide; and
   (d) separating formic acid and at least part of the unreacted formamide from said ethylidene bis-formamide.

3. The process of claim 2 wherein said amount of formic acid is sufficient to make up from ¼ to ⅝ by weight of said reaction mixture.

4. The process of claim 3 wherein said amount of formic acid is sufficient to make up at least about 45 weight percent of said reaction mixture, said mole ratio of formamide to acetaldehyde is in the range of about 4:1 to about 6:1, and said reaction temperature is in the range of about 60° to 85° C.

5. The process of claim 2 wherein said reaction temperature is in the range of 60° to 100° C.

6. The process of claim 4 wherein said reaction mixture is held at said reaction temperature for a time sufficient to convert from 70 to 100 mole percent of said acetaldehyde to ethylidene bis-formamide.

7. The process of claim 2 wherein over 50 weight percent of said acetaldehyde is added after said formamide and said formic acid have been mixed in the minimum proportions required in said reaction mixture.

8. The process of claim 2 wherein said acetaldehyde is added so that said mole ratio of formamide to acetaldehyde is about 4:1 to about 6:1.

9. The process of claim 2 wherein said formic acid and unreacted formamide of step (d) are returned to said reaction mixture.

* * * * *